US010688274B1

(12) United States Patent
Jovanov

(10) Patent No.: US 10,688,274 B1
(45) Date of Patent: Jun. 23, 2020

(54) SYSTEMS AND METHODS FOR MULTI-MODAL AND NON-INVASIVE STIMULATION OF THE NERVOUS SYSTEM

(71) Applicant: Emil Jovanov, Huntsville, AL (US)

(72) Inventor: Emil Jovanov, Huntsville, AL (US)

(73) Assignee: Board of Trustees of the University of Alabama, for and on behalf of the University of Alabama in Huntsville, Huntsville, AL (US)

(*) Notice: Subject to any disclaimer, the term of this patent is extended or adjusted under 35 U.S.C. 154(b) by 184 days.

(21) Appl. No.: 15/605,610

(22) Filed: May 25, 2017

Related U.S. Application Data

(60) Provisional application No. 62/342,096, filed on May 26, 2016.

(51) Int. Cl.
*A61M 21/00* (2006.01)
*A61N 1/04* (2006.01)
(Continued)

(52) U.S. Cl.
CPC ............ *A61M 21/00* (2013.01); *A61H 23/02* (2013.01); *A61N 1/0456* (2013.01); *A61N 1/36025* (2013.01); *A61N 2/002* (2013.01); *A61N 5/0618* (2013.01); *A61M 2021/0016* (2013.01); *A61M 2021/0022* (2013.01); *A61M 2021/0027* (2013.01); *A61M 2021/0044* (2013.01); *A61M 2021/0072* (2013.01); *A61M 2230/005* (2013.01); *A61M 2230/04* (2013.01); *A61M 2230/10* (2013.01); *A61M 2230/63* (2013.01); *A61M 2230/65* (2013.01); *A61N 2005/0626* (2013.01)

(58) Field of Classification Search
None
See application file for complete search history.

(56) References Cited

U.S. PATENT DOCUMENTS 3,497,637 A * 2/1970 Lawrence ............... A61F 11/04
381/23.1
3,659,614 A * 5/1972 Jankelson ............... A61N 1/321
607/139
(Continued)

OTHER PUBLICATIONS

Emily Waltz, "DARPA to Use Electrical Stimulation to Enhance Military Training," http://spectrum.ieee.org/the-human-os/biomedical/devices/.WQnuUvGCyNU.gmail, Apr. 26, 2017.

*Primary Examiner* — Brian T Gedeon
(74) *Attorney, Agent, or Firm* — Maynard Cooper & Gale, P.C.; Jon E. Holland

(57) ABSTRACT

Systems and methods are provided to combine multiple stimulation modalities to significantly increase the effectiveness of non-invasive stimulation. Multiple sensor and stimulation devices and modalities can be combined into a single, compact unit that minimizes the need for additional sensors or stimulation devices. The system features several subunits, referred to as sensory and stimulation devices (SSD), that are integrated into a headphone setup. The system is controlled by a centralized controller that communicates with all of the SSDs and with an external computer system that delivers learning material synchronized with the delivery of stimulations and the collection of user responses based on physiological signals.

20 Claims, 6 Drawing Sheets

(51) Int. Cl.
*A61N 5/06* (2006.01)
*A61N 1/36* (2006.01)
*A61N 2/00* (2006.01)
*A61H 23/02* (2006.01)

(56) References Cited

U.S. PATENT DOCUMENTS

| | | | | |
|---|---|---|---|---|
| 4,638,807 A * | 1/1987 | Ryder | ............... | A61B 5/04085 600/383 |
| 5,318,503 A * | 6/1994 | Lord | ............... | A61M 21/00 600/27 |
| 5,514,175 A * | 5/1996 | Kim | ............... | A61H 39/002 607/115 |
| 6,537,301 B1 * | 3/2003 | Kamei | ............... | A61M 21/00 607/88 |
| 6,556,868 B2 | 4/2003 | Naritoku et al. | | |
| 8,639,343 B2 * | 1/2014 | De Vos | ............... | A61N 1/3601 600/529 |
| 8,914,116 B2 * | 12/2014 | De Vos | ............... | A61H 39/002 607/135 |
| 8,972,024 B2 * | 3/2015 | Walker | ............... | A61H 39/002 607/46 |
| 9,242,092 B2 | 1/2016 | Simon et al. | | |
| 9,248,286 B2 | 2/2016 | Simon et al. | | |
| 9,254,383 B2 | 2/2016 | Simon et al. | | |
| 9,579,060 B1 * | 2/2017 | Lisy | ............... | A61B 5/6803 |
| 9,782,584 B2 * | 10/2017 | Cartledge | ............... | A61N 1/36036 |
| 2005/0165460 A1 * | 7/2005 | Erfan | ............... | A61N 1/326 607/57 |
| 2012/0197355 A1 * | 8/2012 | Braun | ............... | A61M 21/00 607/72 |
| 2014/0316456 A1 * | 10/2014 | Ando | ............... | A61H 7/004 606/204 |
| 2016/0015289 A1 * | 1/2016 | Simon | ............... | A61B 5/04842 600/301 |
| 2016/0235352 A1 * | 8/2016 | DiLorenzo | ............... | A61B 5/04001 |
| 2017/0165485 A1 * | 6/2017 | Sullivan | ............... | A61N 1/36021 |
| 2018/0021564 A1 * | 1/2018 | Goodall | ............... | A61N 2/002 600/379 |
| 2018/0040258 A1 * | 2/2018 | Kouache | ............... | G01C 21/3652 |
| 2018/0256888 A1 * | 9/2018 | Wingeier | ............... | A61N 1/0484 |

* cited by examiner

SYSTEMS AND METHODS FOR MULTI-MODAL AND NON-INVASIVE STIMULATION OF THE NERVOUS SYSTEM

CROSS-REFERENCE TO RELATED APPLICATION

This application claims the benefit of U.S. Provisional Application No. 62/342,096, entitled "Devices and Methods for Multi-Modal Non-Invasive Stimulation of the Autonomous and Central Nervous System" and filed on May 26, 2016, which application is hereby incorporated by reference in its entirety.

BACKGROUND

The present application relates to systems and methods for multi-modal and non-invasive stimulation of the autonomous and central nervous system. More specifically, the present application relates to methods and apparatus for multi-modal augmentation of neural plasticity of the nervous system and modification of the psycho-physiological state of the user.

Electrical stimulation can be used to stimulate brain and nervous system activity for many different purposes. For example, electrical stimulation can be used to attempt to restore memory, increase cognitive function, modify psychophysiological state and for therapeutic purposes. The electrical stimulation can be applied through invasive and non-invasive techniques. Typically, non-invasive techniques are used for the convenience of the patient undergoing the electrical stimulation. Non-invasive techniques can typically involve the placement of electrodes near one or more nerves and/or the brain of the patient. The electrodes can then be used to apply a constant current to the nerves and/or brain in order to change the activity of the nerves and/or brain of the patient to get a desired response. The electrodes may also be used to apply a spatio-temporal activation pattern to the nerves and/or brain of the patient in order to target specific nerves or regions of the brain to obtain a specific response.

When electrical stimulation is being used on a patient, other forms of stimulation (e.g., visual stimulation or audible stimulation) are not typically used or require the use of separate systems having separate controls that are not integrated with the electrical stimulation controls. In addition, when attempting to monitor the results of electrical stimulation (or other stimulations), separate monitoring systems are required that can be cumbersome to the patient and require integration with the electrical stimulation system (or other system being used) in order to be able to identify potential responses to stimulation treatments.

SUMMARY

The present application generally pertains to combining multiple stimulation modalities to significantly increase the effectiveness of non-invasive stimulation. Multiple sensor and stimulation devices and modalities can be combined into a single, compact unit that minimizes the need for additional sensors or stimulation devices. The system features several subunits, referred to as sensory and stimulation devices (SSD), that are integrated into a headphone setup. The system is controlled by a centralized controller that communicates with all of the SSDs and with an external computer system that delivers learning material synchronized with the delivery of stimulation and collection of physiological signals.

Physiological signals can be used to assess the psychophysiological state of the user and to modulate the user's psychophysiological state in order to optimize performance and/or reach an optimum state of activation of the autonomous and central nervous system for the given application. When performing cognitive tasks a user requires an optimum arousal level. If the user's arousal level is too low or too high, the user can have suboptimal cognitive performance. The arousal level of a user can be modified using breathing, audio stimulation (binaural beats), vibration/bone conduction, photic stimulation, and non-invasive stimulation of branches of the vagus nerve. The arousal level of a user can be assessed using a combination of: a) heart rate; b) heart rate variability; c) respiration; d) respiratory sinus arrhythmia (i.e., a change of heart rate caused by respiration); e) galvanic skin response; f) brain electrical activity (e.g., electroencephalogram or EEG); g) pupil dilation; and/or h) vascular tone.

The system and combination of sensors can collect a maximum number of signals in a compact, unobtrusive unit and provide non-invasive stimulation to modulate the physiological state of the user. Optimum sensing and stimulation can be personalized to the user by combining the monitored signals and their features for the optimum assessment of the user's state and stimulation. In one embodiment, a linear combination of individual parameters with weight factors for each feature can be developed for each user. The training process for the system to assess individual weight factors may include the subjective feeling/feedback of the user, as well as, objective measures of the cognitive performance of the user for the given task.

One advantage of the present application is that it can be used for augmentation of cognition, recovery from traumatic brain injury or stroke, implementation of relaxation techniques, and for changing a state of consciousness.

Another advantage of the present application is that it can be used to improve performance or change psychophysiological state of the user.

Other features and advantages of the present application will be apparent from the following more detailed description of the identified embodiments, taken in conjunction with the accompanying drawings which show, by way of example, the principles of the application.

BRIEF DESCRIPTION OF THE DRAWINGS

Wherever possible, the same reference numbers are used throughout the drawings to refer to the same or like parts.

DETAILED DESCRIPTION

Figure 1:
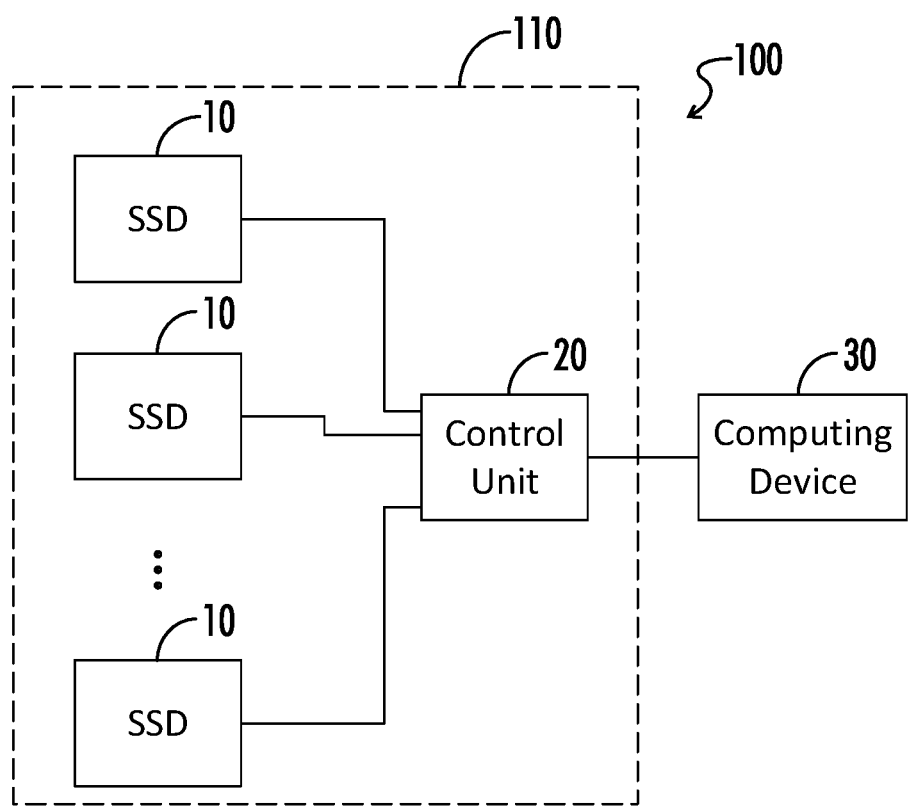
FIG. 1 is a block diagram of an embodiment of a multi-modal sensor and stimulation system.

The present application generally pertains to systems and methods for providing several non-invasive stimulations to a user. The user can place a device (e.g., headgear) on the user's head to receive the non-invasive stimulations. The headgear can incorporate several different types of sensory and stimulation devices (SSDs) to provide the stimulations to the user. The different types of stimulation can include electrical stimulation, audio stimulation, photic stimulation, vibration stimulation, olfactory stimulation and electromagnetic stimulation. In addition to providing stimulation to the user, the headgear can also include different sensors to measure different physiological parameters of the user. The sensors of the headgear can be used to measure the electroencephalogram, the electrocardiogram, the photoplethysmogram, the electrooculagram and/or the balistocardiograph of the user. Using the measurements from the sensors, different physiological parameters of the user can be determined such as brain activity, heart rate, blood pressure, respiration rate, etc., to assess activity of central and autonomous nervous system.

The headgear worn by the user can include a top headband that is positioned on top of the user's head and a front headband that is positioned on the user's forehead. Each of the headbands can include electrical contacts that can be used to provide both electrical stimulation to the user and to measure physiological parameters of the user. In addition, the headgear can include ear pads that are placed over the ears of the user. The ear pads can include both an ear bud placed in the ear and an SSD that is placed behind the ear. The ear bud can be used to provide audio stimulation to the user and can include a stimulation device that can be used to provide electrical stimulation to a branch of the vagus nerve. The behind the ear SSD can include electrodes that are placed in contact with both the ear of the user and the head of the user to provide both electrical stimulation to the user and to measure physiological parameters of the user. The behind the ear SSD can also include a reference electrode that is in contact with the user to provide a reference when measuring a physiological parameter of a user. The behind the ear SSD can also include a pulse oximeter in contact with the lobule of the user and a vibration device that is in contact with the user to provide vibration stimulation to the user.

All of the sensors and stimulation devices of the head gear can be in communication with a control unit. The control unit can be integrated into the headgear or can be in a separate housing that is coupled to the headgear. The control unit can send signals to and receive signals from each of the SSDs. The control unit can be in communication with a central computer that controls the operation of the SSDs of the head gear. The central computer can provide instructions to the control unit to implement a variety of different stimulation sequences to the user, including instructions to provide targeted electrical stimulation to certain areas of the brain. As the control unit receives the sensor measurements from the SSDs, the control unit can provide the measurements to the central computer. The central computer can then evaluate the user's response to the stimulations and make adjustments to the stimulations in order to achieve the desired results. Some adjustments that can be made to the stimulations include increasing or decreasing the duration of the stimulation, increasing or decreasing the magnitude of the stimulation and/or adding or removing particular types of stimulations.

In addition, the central computer can determine an arousal level of the user, which can be used to optimize the user's cognitive learning. The arousal level of the user can be determined with a combination of physiological parameters determined from the measurements of the sensors in the headgear. The physiological parameters may or may not be weighted when determining arousal level for the user. If the physiological parameters are weighted, then each individual user may have a different set of weights in order to determine that user's optimal arousal level. Further, the central computer can customize stimulation sequences for each user in order to maximize the user's benefit from the treatment.

FIG. 1 shows a block diagram embodiment of a multi-modal sensor and stimulation system 100. The multi-modal sensor and stimulation system 100 can include a user-wearable device 110 and a computing device 30 coupled to the device 110. The device 110 can include one or more sensory and stimulation devices (SSDs) 10 that can provide different types of stimulation to the user and measure the user's response to the different stimulations. The SSDs 10 can be coupled to a control unit 20 incorporated into the device 110. The control unit 20 can send instructions or signals to the SSDs 10 to control the operation of the SSDs 10. The control unit 20 can also receive data and/or signals from the SSDs 10 indicating the user's response to the stimulations. The control unit 20 can be coupled to the computing device 30 to receive instructions from the computing device 30 for the SSDs 10 and to provide data from the SSDs 10 to the computing device 30. In one embodiment, the control unit 20 can communicate wirelessly (i.e., via electromagnetic or acoustic waves carrying a signal) with the computing device 30, but in other embodiments, it is possible for the control unit 20 to communicate with the computing device 30 over a conductive medium (e.g., a wire), fiber, or otherwise.

Figure 2:
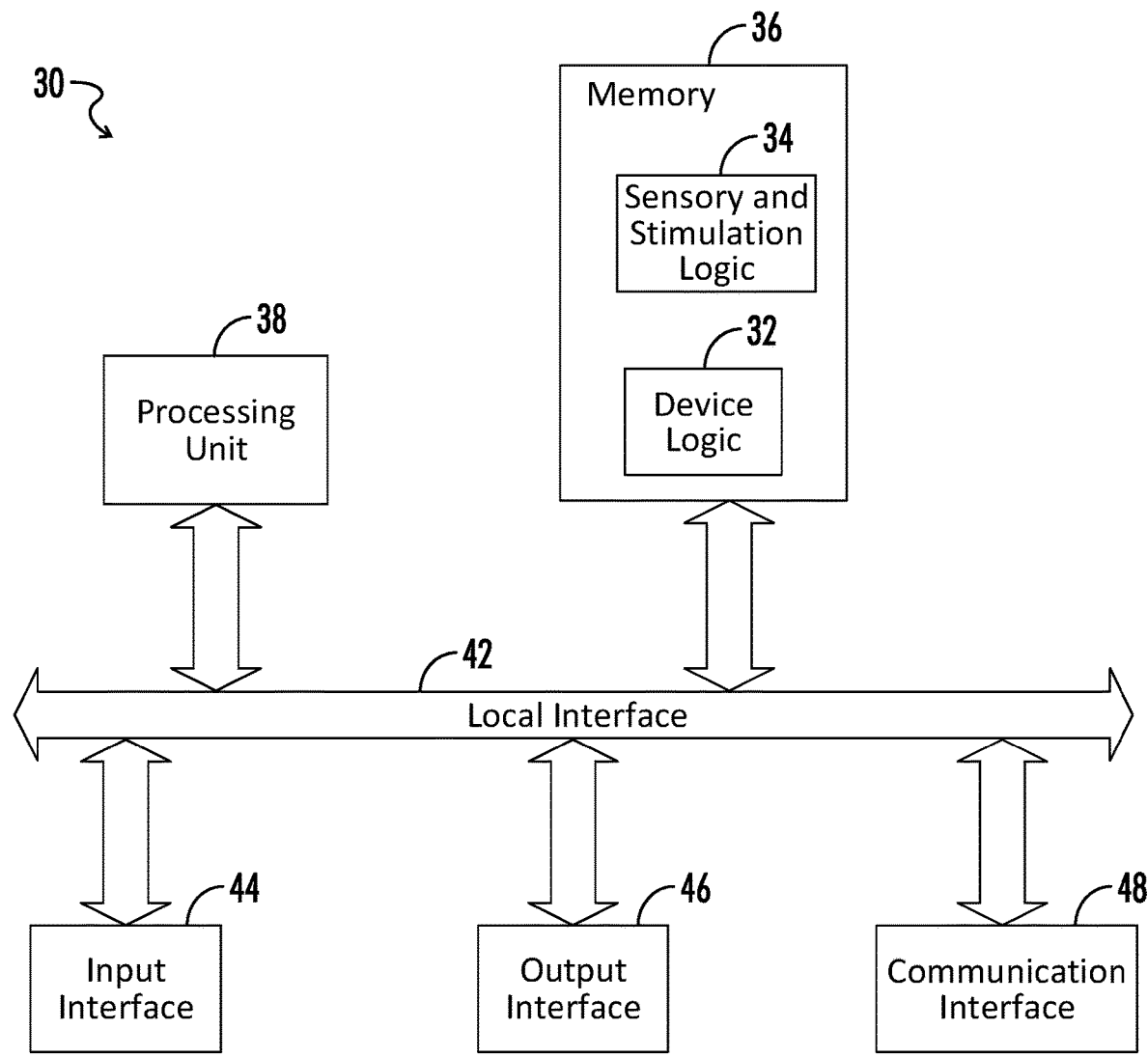
FIG. 2 is a block diagram of an embodiment of a computing device of the multi-modal sensor and stimulation system of FIG. 1.

FIG. 2 shows an embodiment of the computing device 30. The computing device 30 may be implemented as one or more general or special-purpose computers, such as a laptop, hand-held (e.g., smartphone), desktop, or mainframe computer. The computing device 30 can include logic 32, referred to herein as "device logic," for generally controlling the operation of the computing device 30, including communicating with the control unit 20. The computing device 30 also includes sensory and stimulation logic 34 to control the operation of the SSDs 10 and to process the data and information measured by the SSDs 10. The device logic 32 and the sensory and stimulation logic 34 can be implemented in software, hardware, firmware or any combination thereof. In the computing device 30 shown in FIG. 3, the device logic 32 and the sensory and stimulation logic 34 are implemented in software and stored in memory 36 of the computing device 30. Note that the device logic 32 and the sensory and stimulation logic 34, when implemented in software, can be stored and transported on any non-transitory computer-readable medium for use by or in connection with an instruction execution apparatus (e.g., a microprocessor) that can fetch and execute instructions. In the context of this application, a "computer-readable medium" can be any device, system or technique that can contain or store a computer program for use by or in connection with an instruction execution apparatus.

The computing device 30 includes at least one conventional processing unit 38, which has processing hardware for executing instructions stored in memory 36. As an example, the processing unit 38 may include a digital signal processor or a central processing unit (CPU). The processing unit 38 communicates to and drives the other elements within the computing device 30 via a local interface 42, which can include at least one bus. Furthermore, an input interface 44, for example, a keyboard, a mouse, touchscreen, sensor or any other interface device or apparatus, can be used to input data from a user of the computing device 30, and an output interface 46, for example, a printer, monitor, liquid crystal display (LCD), or other display apparatus, can be used to output data to the user of the computing device 30. Further, a communication interface 48, such as at least one modem, may be used to communicate with control unit 20.

Figure 3:
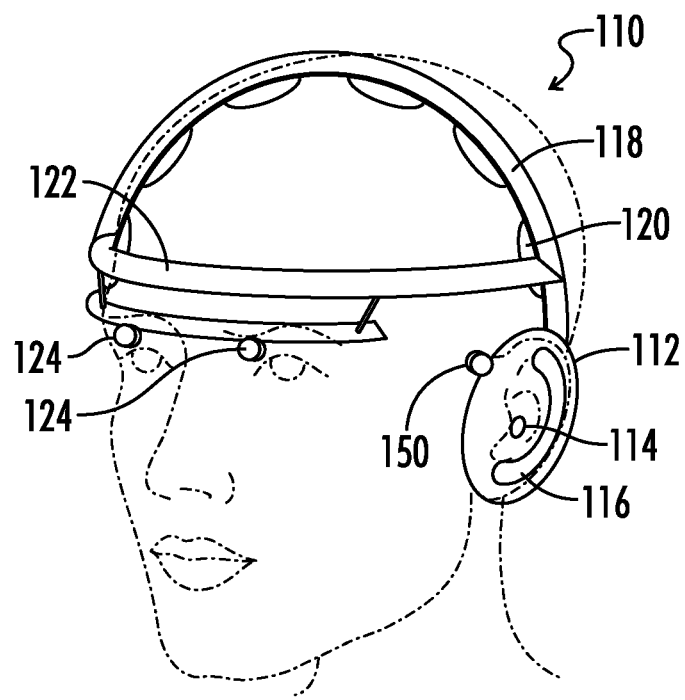
FIG. 3 is an embodiment of the user wearable device of the multi-modal sensor and stimulation system of FIG. 1.

FIG. 3 shows an embodiment of a user-wearable device 110. In one embodiment, as shown in FIG. 3, the device 110 can be a type of headgear that is worn on the head of the user. However, in other embodiments, different configurations of the device 110 can be used. The device 110 can include headphone pads 112 that are placed in proximity to one or both of the ears of the user. In one embodiment, the headphone pads 112 can be circumaural pads that surround the ear. However, in other embodiments, different configurations of the headphone pads 112 (e.g., supra-aural) can also be used. The headphone pads 112 can incorporate one or both of speakers or earbuds 114 (that operate as an SSD), one or more trigeminal SSDs 150 located near the temple between the ear and eye, and one or more auricular SSDs 116 located behind the ear. The device 110 can include a top headband 118 with one or more electrodes 120 that can provide electrical stimulation to the top of the head of the user and a front headband 122. In one embodiment, the front headband 122 can include one or more photic SSDs 124 to provide photic stimulation to one or both of the user's eyes. In another embodiment, the photic SSDs 124 can be integrated into (or connected to) eyewear that is worn by the user. In other embodiments, the front headband 122 can include a virtual/augmented reality display or a screen/projection unit. In still other embodiments, the front headband 122 can include one or more electrodes (not shown) to provide electrical stimulation and/or a SSD (not shown) that can provide olfactory stimulation and monitoring.

Figure 4:
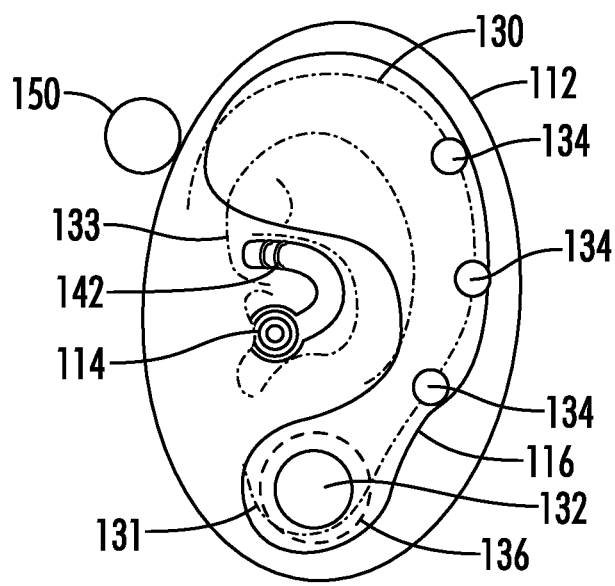
FIG. 4 is an embodiment of the interior components of the headphone pad of the user-wearable device of FIG. 3 relative to a user's ear.
Figure 5A:
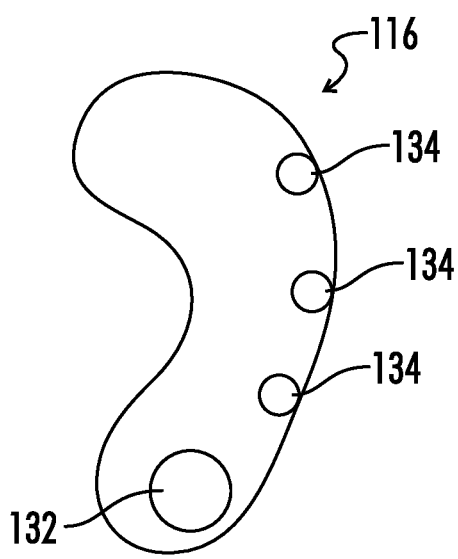
FIG. 5A is a front view of an embodiment of the auricular SSD from FIG. 4.
Figure 5B:
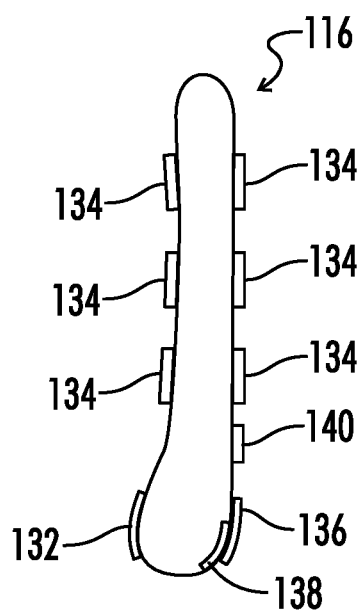
FIG. 5B is a side view of an embodiment of the auricular SSD from FIG. 4.
Figure 5C:
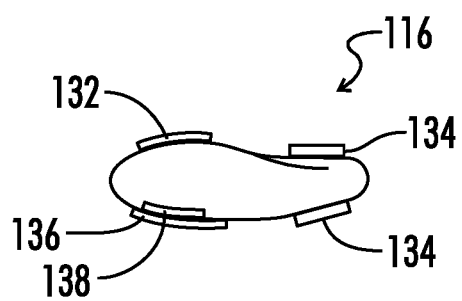
FIG. 5C is a bottom view of an embodiment of the auricular SSD from FIG. 4.

FIG. 4 shows an embodiment of the interior components of the headphone pad 112 relative to a user's ear. As shown in FIG. 4, the auricular SSD 116 can be located behind the ear lobe 130 of the user. In one embodiment, the auricular SSD 116 can be a soft anatomically shaped device that can comfortably reside behind the ear of the user for prolonged periods of time. In another embodiment, the auricular SSD 116 can have an arcuate shape to fit behind the ear of the user. As shown in FIGS. 5A-5C, the auricular SSD 116 can include a photoplethysmogram (PPG) sensor 132 (e.g., a pulse oximeter) to measure the PPG of the user. The PPG represents blood volume pulse and can be used to measure or assess: a) heart rate (HR); b) heart rate variability (HRV); c) breathing rate (BR); and d) vascular tone using blood volume pulse or pulse travel time (PIT) as a latency of the PPG peak from the R peak in an electrocardiogram (ECG). The PPG sensor 132 can be implemented on the front of the auricular SSD 116 to allow good contact with the lobule 131 (see FIG. 2) of the ear, which is a location that can be used for PPG sensing.

The auricular SSD 116 can also include one or more electrical contacts (or electrodes) 134 for the monitoring of heart activity (e.g., an ECG), brain electrical activity (e.g., an electroencephalogram (EEG)), or galvanic skin response (GSR). The electrodes 134 can be located on one or both sides of the auricular SSD 116 to contact either a portion of the user's ear or a portion of the user's head (e.g., the temporal bone or the mastoid bone). An electrical contact (or electrode) 136 for the EEG reference can be located at the bottom of the auricular SSD 116 in contact with the mastoid bone or the lobule 131. A vibrator or speaker 138 can be used to apply stimulation using bone conduction. An accelerometer 140 can be used for detection of a balistocardiograph (BCG) representing motion caused by the mechanical movement of the heart. In one embodiment, the delay between the BCG and the PPG is a function of vascular tone/blood pressure and can be used to assess the arousal of the user.

The trigeminal SSD 150 can be attached to the exterior of the headphone pad 112 in one embodiment. However, in other embodiments, the trigeminal SSD 150 can be incorporated within the headphone pad 112 such that the headphone pad 112 has an enlarged region enclosing the trigeminal SSD 150. In still other embodiments, the trigeminal SSD 150 can be integrated into the front headband 122. The trigeminal SSD 150 can include one or more electrodes that are positioned near the temple to provide electrical stimulation to branches of the trigeminal nerve.

The earbud 114 can be a soft anatomically shaped device that can comfortably reside in the ear with good contact with the cymba concha region 133 of the ear. Acoustic stimulation can be delivered through a speaker in the earbud 114 and the electrical stimulation of branches of the vagus nerve (VNS stimulation) can be delivered through electrical contacts 142 of a stimulator that resides on soft extension of the earbud 114 designed to fit the anatomical shape of the cymba concha region. While not shown in FIGS. 3 and 4, the control unit 20 can be incorporated in the headphone pad 112. However, in other embodiments, the control unit 20 may be incorporated into other portions of the device 110 (e.g., top headband 118).

Referring back to FIG. 3, the top headband 118 can integrate EEG sensors with stimulation electrodes 120. In one embodiment, the placement of the sensors/stimulation electrodes 120 can follow standard EEG electrode placements, such as the international 10-20 system. The photic SSDs 124 can be integrated into a separate band near the eyes of the user, integrated into the front headband 122, into eyeglasses or virtual reality goggles, or implemented as a modulation of the virtual or augmented personal display. The photic SSDs 124 can provide cues for the pacing of the user's breathing or generate a Steady State Visual Evoked Response (SSVER) from the user. The SSVER can be recorded with the behind the ear SSD device 116 or by sensors in the front headband 122 and used to assess the focused attention of the user. Olfactory stimulation can be implemented in a separate band close to the nose of the user or integrated into the other parts of the system, such as the front headband 122 or a virtual reality display. Olfactory stimulation can be controlled by the central computer 30 (see FIG. 1) to provide an emotional response as a "reward" for successful execution of a task to strengthen learning by subliminal stimulation.

In one embodiment, magnetic field stimulation can be integrated into the device 110 by using coils instead of electrodes in one or more of the top headband 118, the front headband 122 and the auricular SSD 116.

The device 110 can be used to detect one or more the following signals from a user: an electroencephalogram (EEG); an electrooculagram (EOG); a photoplethysmogram (PPG); and a balistocardiogram (BCG). In other embodiments, the device 110 can be used to detect other signals from the user. The detected signals can be provided to the control unit 20, which can then send the signals to the computing device 30 for processing by the sensory and stimulation logic 34. The EEG can be detected with electrodes in one or more of the top headband 118, the front headband 122, and the auricular SSD 116. The EOG can be detected with the photic SSDs 124 and/or the front headband 122. The PPG can be detected with the PPG sensor 132. The BCG can be detected with accelerometer 140.

The device 110 and the computing device 30 can also be used to detect the following physiological parameters from a user: brain electrical activity using EEG; steady state evoked potentials (SSVEP) or steady state evoked response (SSVER); eye movement and blinking using EOG; heart rate using ECG, PPG and/or BCG; heart rate variability (HRV) using ECG and/or PPG; vascular tone (i.e., the time delay between ECG/BCG and PPG for each heart beat); galvanic skin response (GSR); respiration rate and effort from PPG; respiratory sinus arrhythmia (i.e., the change of heart rate or inter-beat intervals caused by respiration) using respiratory effort and RR intervals (i.e., the interval between successive Rs in the QRS complex of the ECG wave); blood pressure assessed using latency between ECG and PPG/BCG; and arousal as a personalized weighted combination of the above parameters. In other embodiments, the device 110 and the computing device 30 can be used to detect other physiological parameters from the user.

The sensory and stimulation logic 34 can provide signals or commands to the control unit 20 of the device 110 for one or more of the following stimulation types: electrical stimulation; audio stimulation; vibration stimulation; photic stimulation; olfactory stimulation; and electromagnetic field stimulation. In one embodiment, electromagnetic field stimulation can be integrated into the device 110 by using coils instead of electrodes in one or more of the top headband 118, the front headband 122 and the auricular SSD 116. Olfactory stimulation can be implemented into the device 110 using a separate band close to the nose of the user or integrated into the other parts of the system, such as the front headband 122 or a virtual reality display. Olfactory stimulation can be controlled by the central computer 30 (see FIG. 1) to provide an emotional response as a "reward" for successful execution of a task to strengthen learning by subliminal stimulation.

Photic stimulation may directly drive the visual cortex and create steady state visual evoked potentials across the cortex that can be measured and analyzed using EEG electrodes in the top headband 118, the front headband 122 and the auricular SSD 116. Vibration stimulation can provide similar binaural beats stimulation or direct stimulation at the target frequency (e.g., at the frequency of targeted brain electrical activity) using the vibrational device 138. Audio stimulation using the earbud 114 can use binaural beats to generate brain electrical activity at the precise frequency of the difference in frequencies between the left and right ear.

The system 100 can implement electrical stimulation in the user as one or more of current stimulation with a constant or variable current (e.g., transcranial direct current stimulation or tDCS), voltage stimulation with a constant voltage or charge stimulation. Charge based stimulation can be used to create biological effects. A switched capacitor circuit is used to generate a precise charge and then apply it to selected electrodes for stimulation.

Figure 6:
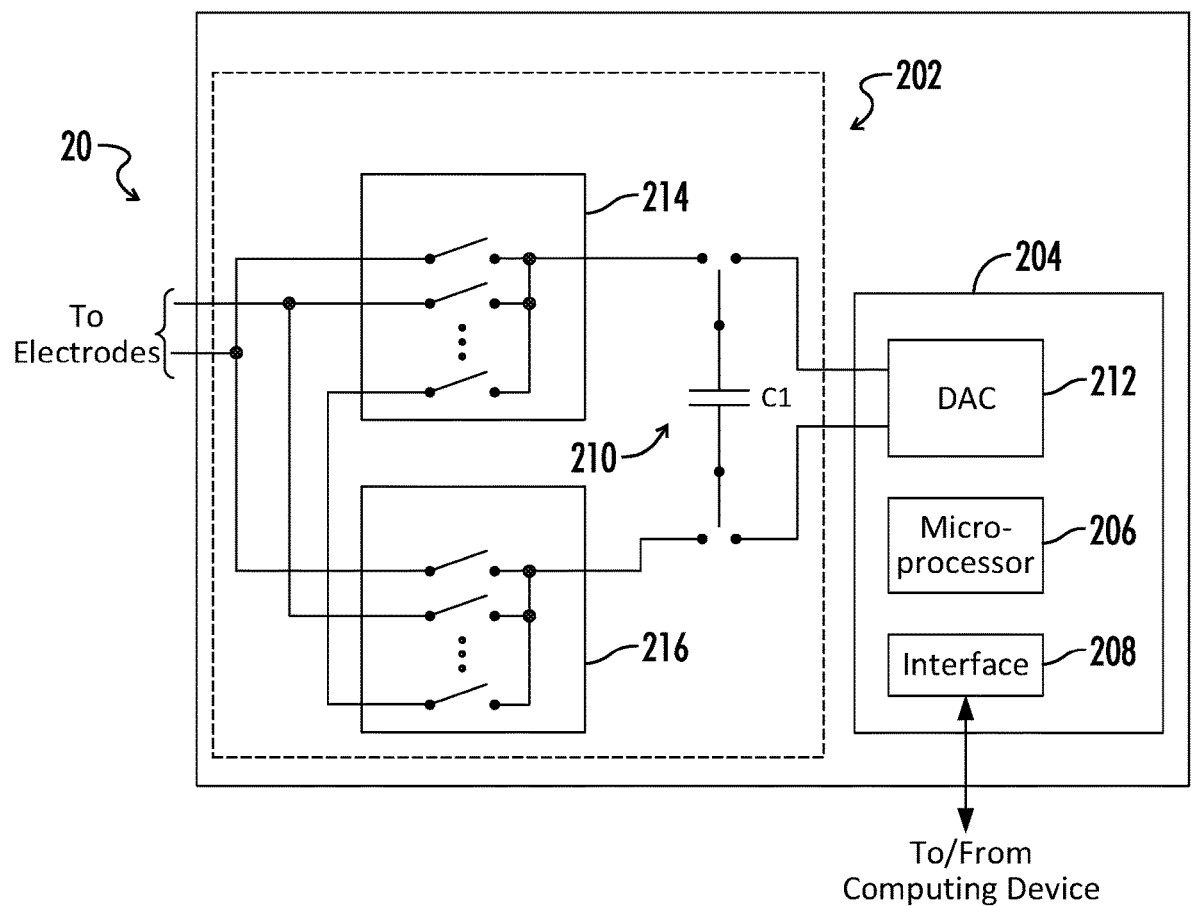
FIG. 6 is a block diagram of an embodiment of the control unit of FIG. 1 with switched capacitor charge stimulation device.

FIG. 6 shows of an embodiment of the control unit 20 with a switched capacitor charge stimulation circuit or stimulator 202 controlled by a controller 204. The controller 204 can control the stimulator 202 in real-time with a microprocessor 206 that communicates with the computing device 30 through interface 208. Microprocessor 206 controls switches of a switched capacitor 210 to charge or discharge a capacitor C1. During charging of the capacitor C1, the switched capacitor 210 is connected to the digital to analog converter (DAC) 212 that generates an appropriate voltage as instructed by the microprocessor 206. The voltage provided by the DAC 212 can be either positive or negative, depending on the required stimulation and the corresponding electrodes selected to apply the stimulation. The total charge (Q) on the capacitor C1 of the switched capacitor 210 can be based on the output voltage (V) from the DAC 212 and the capacitance (C) of the capacitor C1. In one embodiment, the total charge Q for the capacitor C1 can be determined by multiplying the output voltage V by the capacitance C.

Before applying the stimulation, the microprocessor 206 can control a first analog multiplexer 214 and a second analog multiplexer 216 to select the electrodes to receive stimulation. In one embodiment, the electrodes can be located in one or more of the top headband 118, the front headband 122 and the auricular SSD 116. As shown in FIG. 6, the stimulator 202 has leads or connections for two electrodes, but the stimulator 202 may have leads or connections for one electrode or more than two electrodes in other embodiments depending on the requirements of the application and the number of outputs in the first and second analog multiplexers 214, 216.

Figure 7:
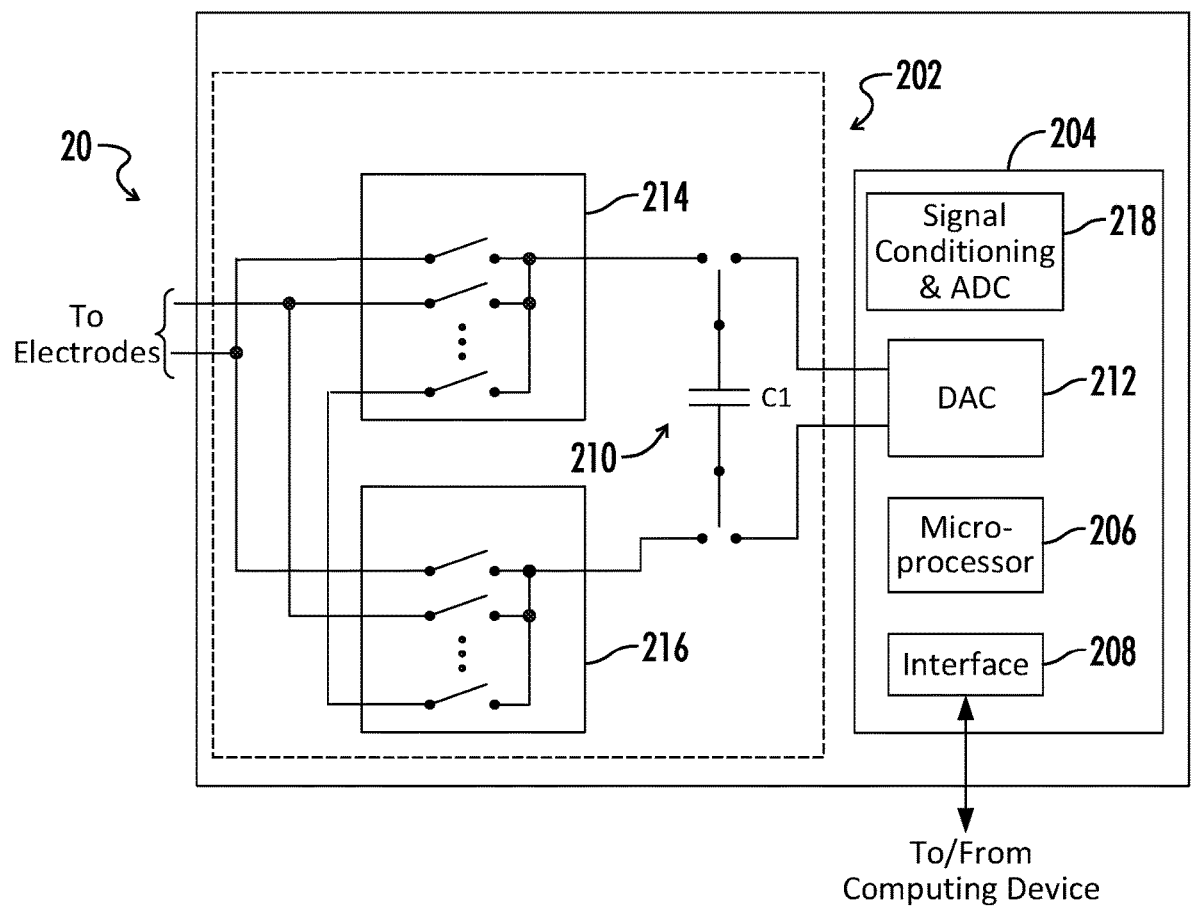
FIG. 7 is a block diagram of an embodiment of the control unit of FIG. 1 with a switched capacitor charge stimulation device with monitoring of the stimulation site.

FIG. 7 shows of an embodiment of the control unit 20 with a switched capacitor charge stimulation circuit or stimulator 202 with monitoring of the stimulation site. For some applications, stimulation can be enhanced by applying stimulation synchronized with the native activity of the nervous system. Thus, monitoring of the stimulation site may be required in order to effectively perform the stimulation. Similar to the embodiment shown in FIG. 6, the stimulator 202 can be connected to the controller 204. However, in the embodiment of FIG. 7, the controller 204 can include a signal conditioning circuit and analog to digital converter (ADC) 218 that is controlled by the microprocessor 206.

The signal conditioning circuit and ADC 218 can be connected to the stimulation side of the switched capacitor 210. By having the signal conditioning circuit and ADC 218 connected to the microprocessor 206, the microprocessor 206 can monitor the voltage between selected electrodes before and after a stimulation caused by connecting the capacitor C1 to the corresponding electrodes. After reviewing the corresponding voltage between the electrodes, the microprocessor 206 can adjust the charge provided to the switched capacitor 210 by the DAC 212 in order to get a desired voltage between the electrodes.

In one embodiment, the system 100 can be used to create spatio-temporal activation patterns of stimulation using software controlled stimulation with charges of different intensity and polarity occurring at different times and in different electrodes. The sensory and stimulation logic 34 of computing device 30 can be used to create the spatio-temporal patterns and to control the intensity, polarity and timing of the charges provided by the stimulator 202 to the electrodes via communications with the controller 204. In addition, the sensory and stimulation logic 34 of computing device 30 can be used to provide stimulations at specific times and specific locations in the device 110 to obtain a better localization or focus of stimulation in the brain and nervous system. For example, specific electrodes in the top headband 118, the front headband 122, the trigeminal SSD 150 and the auricular SSD 116 can be used to obtain a more focused stimulation of a region of the brain or nervous system.

In one embodiment, the system 100 can facilitate non-invasive stimulation with real-time monitoring of users for numerous applications. For example, the possible applications for the system 100 can include improving neural plasticity, improving cognitive performance and providing relaxation techniques. To improve neural plasticity, the system 100 can provide a multi-modal, personalized combination of stimulations combined with the delivery of new material, or new exercise. Some examples can include learning or rehabilitation, such as stroke or traumatic brain injury rehabilitation. Other applications also include treatment of the post-traumatic stress disorder desensitization and reprocessing.

To improve cognitive performance, the system 100 can perform real-time monitoring of signals that allows the real-time assessment of the arousal of the user, while providing different stimulation modalities to facilitate modulation of arousal and overall psychophysiological state by keeping the user "in the zone."

To provide relaxation techniques, the system 100 can provide multimodal stimulation and physiological entrainment to create deeply relaxed state in the user. Binaural beat entrainment using natural sounds can be combined with photic stimulation to transition the brain electrical activity of the user from Alpha to lower Alpha and Theta. Photic stimulation can create entrainment of breathing from the natural initial state as detected using sensors to a relaxed, slower, and deeper breathing. Optical stimulation can provide cues for breathing phases. The monitoring of the heart rate, heart rate variability, and respiratory sinus arrhythmia can provide assessment of strain to optimize basic physiology (breathing and heart rate) to the optimum level for the current state of the user. Closed loop control, entrainment, and stimulation by the system 100 can facilitate modification of the physiological state of the user in minimum time.

In one embodiment, the system 100 can be used to implement an interval performance boost methodology. The interval performance boost methodology can include a presentation phase, a learning phase and a consolidation phase. The presentation phase combines stimulations for a personalized optimization of the user's arousal to improve the user's cognitive performance and focused attention. The learning phase uses stimulation of memorization and repetition of the most important concepts to be learned by the user. The consolidation phase can create a deeply relaxed state with heightened awareness in the user by using sensory withdrawal with brain entrainment to consolidate the new material to be learned by the user.

In one embodiment, the multi-modal stimulations provided by the system 100 may be user-configurable. A user of the system may select the modes of stimulation to be performed on the user and may select the amounts (or percentages) that the selected stimulations are applied to the user. Once the user has selected the modes and amounts of stimulation, the computing device 30 can develop a stimulation regimen for the user based on the user-configured parameters. For example, a user may select to receive electrical stimulation for 50% of the regimen, audio stimulation for 30% of the regimen and photic stimulation for 20% of the regimen while foregoing other types of stimulation. In another embodiment, relative percentage of intensity of individual modalities might be selected according to user's preferences.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. A user-wearable device to provide stimulation to the nervous system of a user, the device comprising:
   a headband configured to be worn on a head of the user, the headband comprising at least one electrode configured to provide electrical stimulation to the user; and
   a headphone pad coupled to the headband and positioned in proximity to an ear of the user, the headphone pad comprising:
      a first sensory and stimulation device (SSD) configured to provide a first type of stimulation to the user; and
      a second SSD configured to provide a second type of stimulation to the user, wherein the second type of stimulation provided by the second SSD is different from the first type of stimulation provided by the first SSD, the second SSD comprising a sensor positioned in contact with the ear of the user to measure a physiological parameter of the user,
      wherein the electrical stimulation provided by the at least one electrode, the first type of stimulation provided by the first SSD and the second type of stimulation provided by the second SSD are adjustable by a control unit in response to the measured physiological parameter of the user to obtain a preselected arousal level from the user.

2. The device of claim 1, wherein the headband is a first headband and the device further comprises a second headband coupled to the first headband and configured to be worn on the forehead of the user, the second headband comprising a third SSD configured to provide a third type of stimulation to the user.

3. The device of claim 2, wherein the at least one electrode is an at least one first electrode, the third SSD comprises at least one of a photic SSD or at least one second electrode, the photic SSD coupled to the second headband and positioned in proximity to an eye of the user, the photic SSD configured to provide photic stimulation to the user, and the at least one second electrode configured to provide electrical stimulation to the user.

4. The device of claim 1, further comprising a third SSD positioned in proximity to an eye of the user and configured to provide photic stimulation to the user.

5. The device of claim 1, further comprising a computing device in communication with the control unit, the computing device configured to generate commands to the control unit to control operation of the at least one electrode, the first SSD and the second SSD.

6. The device of claim 1, wherein the first SSD comprises an earbud positioned in proximity to the cymba concha region of the ear, the earbud configured to provide acoustic stimulation to the user.

7. The device of claim 6, wherein the earbud comprises an extension portion having at least one electrical contact, the at least one electrical contract configured to provide electrical stimulation to a branch of a vagus nerve.

8. The device of claim 1, further comprising a third SSD positioned in proximity to a nose of the user and configured to provide olfactory stimulation to the user.

9. The device of claim 1, wherein the at least one electrode is an at least one first electrode, the second SSD is positioned behind the ear of the user, the second SSD having a first side and a second side opposite the first side, the second SSD comprises at least one second electrode positioned on at least one of the first side of the second SSD or the second side of the second SSD, the at least one second electrode configured to provide electrical stimulation to the user.

10. The device of claim 9, wherein the at least one second electrode comprises a first plurality of second electrodes positioned on the first side of the second SSD for contacting the ear of the user and a second plurality of second electrodes positioned on the second side of the second SSD for contacting a head of the user.

11. The device of claim 9, wherein the headphone pad further comprises a third SSD positioned on an exterior portion of the headphone pad, the third SSD comprising at least one third electrode configured to provide electrical stimulation to the user, wherein one or more of the at least one first electrode, the at least one second electrode and the at least one third electrode are controllable by the control unit to apply a spatio-temporal activation pattern to the user to focus stimulation on an area of a brain of the user.

12. The device of claim 9, wherein the at least one second electrode is configured to monitor at least one of heart activity, brain electrical activity or galvanic skin response of the user.

13. The device of claim 12, wherein the control unit is configured to adjust the electrical stimulation provided by the at least one electrode, the first type of stimulation provided by the first SSD and the electrical stimulation provided by the at least one second electrode in response to the measured physiological parameter of the user and the monitored at least one of heart activity, brain electrical activity or galvanic skin response.

14. The device of claim 1, wherein the at least one electrode is an at least one first electrode, the headphone pad further comprises a third SSD positioned on an exterior portion of the headphone pad, the third SSD comprising at least one second electrode configured to provide electrical stimulation to the user.

15. The device of claim 1, wherein the second SSD comprises a vibrational device configured to apply stimulation using bone conduction.

16. The device of claim 1, wherein the control unit is configured to adjust at least one of the electrical stimulation, the first type of stimulation or the second type of stimulation by increasing or decreasing the duration of the corresponding stimulation.

17. The device of claim 1, wherein the control unit is configured to adjust at least one of the electrical stimulation, the first type of stimulation or the second type of stimulation by increasing or decreasing the magnitude of the corresponding stimulation.

18. The device of claim 1, wherein the sensor is positioned to contact a lobule of the ear of the user and configured to measure a photoplethysmogram of the user.

19. A system to provide stimulation to the nervous system of a user, the system comprising:
    a headband configured to be worn on a head of the user, the headband comprising at least one electrode configured to provide electrical stimulation to the user;
    a headphone pad coupled to the headband and positioned in proximity to an ear of the user, the headphone pad comprising:
        a first sensory and stimulation device (SSD) configured to provide a first type of stimulation to the user; and
        a second SSD configured to provide a second type of stimulation to the user, wherein the second type of stimulation provided by the second SSD is different from the first type of stimulation provided by the first SSD, the second SSD comprising a sensor positioned in contact with the ear of the user to measure a physiological parameter of the user; and
    a control unit in communication with the at least one electrode, the first SSD, and the second SSD, the control unit configured to adjust the electrical stimulation provided by the at least one electrode, the first type of stimulation provided by the first SSD and the second type of stimulation provided by the second SSD in response to the measured physiological parameter of the user to obtain a preselected arousal level from the user.

20. The system of claim 19, wherein the control unit is configured to receive the measured physiological parameter of the user from the sensor, evaluate the measured physiological parameter to determine an arousal level of the user, and calculate an adjustment to the electrical stimulation provided by the at least one electrode, the first type of stimulation provided by the first SSD and the electrical stimulation provided by the at least one second electrode based on the determined arousal level of the user.

* * * * *